(12) United States Patent
Grondin et al.

(10) Patent No.: US 10,941,131 B1
(45) Date of Patent: Mar. 9, 2021

(54) CONVERSION OF CANNABIDIOL OR DELTA-9 TETRAHYDROCANNABINOLIC ACID TO DELTA-9 TETRAHYDROCANNABINOL AND DELTA-8 TETRAHYDROCANNABINOL IN NONTOXIC HETEROGENEOUS MIXTURES

(71) Applicant: Pure Tonic Concentrates, LLC, Reno, NV (US)

(72) Inventors: Richard A. Grondin, Fallon, NV (US); Jacob R. Ward, Reno, NV (US)

(73) Assignee: Pure Tonic Concentrates, LLC, Reno, NV (US)

( * ) Notice: Subject to any disclaimer, the term of this patent is extended or adjusted under 35 U.S.C. 154(b) by 0 days.

(21) Appl. No.: 16/665,926

(22) Filed: Oct. 28, 2019

(51) Int. Cl.
 *C07D 311/80* (2006.01)
(52) U.S. Cl.
 CPC .................................. *C07D 311/80* (2013.01)
(58) Field of Classification Search
 CPC .................................................... C07D 311/80
 See application file for complete search history.

(56) References Cited

U.S. PATENT DOCUMENTS

2004/0143126 A1 7/2004 Webster et al.

FOREIGN PATENT DOCUMENTS

WO WO-02070506 A2 * 9/2002 ........... C07D 311/80

* cited by examiner

*Primary Examiner* — John S Kenyon
(74) *Attorney, Agent, or Firm* — Glass and Associates; Kenneth D'Alessandro; Kenneth Glass

(57) ABSTRACT

A solvent-free method for converting CBD or delta-9 THC-A to delta-9 THC and delta-8 THC includes adding CBD to a reaction vessel, streaming an inert gas through the reaction vessel, heating the CBD while stirring to melt the CBD, stirring the melting CBD, adding concentrated hydrochloric acid as a catalyst to the melting CBD while stirring, increasing the temperature over time to a temperature not to exceed the boiling point of reactants and products in the reaction vessel, holding the reaction vessel at a temperature less than the boiling point temperature for the reactants and products in the reaction vessel for an amount of time to allow the complete conversion of the CBD, and bubbling an inert gas into the reaction products to remove free ions of hydrogen and chloride. The CBD can be replaced in whole or in part by delta-9 THC-A as the reactant.

24 Claims, 6 Drawing Sheets

Dibenzopyran Numbering System ed States Patent Application Publication No. US 2004/0143126 A1.
CONVERSION OF CANNABIDIOL OR DELTA-9 TETRAHYDROCANNABINOLIC ACID TO DELTA-9 TETRAHYDROCANNABINOL AND DELTA-8 TETRAHYDROCANNABINOL IN NONTOXIC HETEROGENEOUS MIXTURES The present invention relates to conversion of cannabidiol (CBD) to delta-9 tetrahydrocannabinol (delta-9 THC) and delta-8 tetrahydrocannabinol (delta-8 THC). More particularly, the present invention relates to conversion of CBD to delta-9 THC and delta-8 THC in heterogeneous and solvent-free mixtures.

BACKGROUND

In the present environment inclusion of the more popular cannabinoid compounds is rapidly increasing in many parts of the USA as well as in other countries around the world. Today these include 33 states plus the District of Columbia allowing for the medicinal cultivation, production, sale and consumption of *cannabis* products with a doctor's prescription. In ten of these same states and the District of Columbia cultivation of *cannabis* is also permitted for the production, sale and consumption of recreational *cannabis* products. The 2018 farm bill passed by congress allows for hemp-based products to be legal in all 50 states plus the District of Columbia provided the total tetrahydrocannabinol (THC) content does not equal or exceed 0.3% threshold.

In other parts of the world 19 countries to date including Australia, Canada, Israel, New Zealand, Thailand, parts of the European Union, and South America have some form of legalization of *cannabis* whether medicinal or recreational. Still other countries have more restrictive laws that require only a very limited list of *cannabis*-based pharmaceutical drugs that can be prescribed. Marinol, Dronabinol, Nabilone, Sativex or Epidiolex are presently known and more are under development by pharmaceutical companies. Many other countries remain cautiously optimistic about legalizing *cannabis* while a few countries with very conservative governments remain steadfast in the criminality of *cannabis* or hemp products.

In view of this positive and somewhat explosive paradigm shift in societies tolerance and acceptance of a previously universally prohibited illegal plant, not only are both hemp and *cannabis* along with their extracted contents accepted but variations of the components of *cannabis* plants including cannabinoids, terpenoids and flavoids are also accepted for various psychotropic and non-psychotropic effects upon consumption.

In the prior-art there exists the disadvantage that commonly-used synthetic routes require and produce unwanted compounds which can corrupt the overall desired purity and yield. These impurities require a certain amount of time and expense to separate from the desired products. The degree to which impurities remain in the final product has an adverse effect on the overall yield, making it difficult and expensive to achieve a final targeted purity and still maintain a reasonable yield.

Prior art processes for converting cannabidiol (CBD) to delta-9 THC and/or delta-8 THC require the need for multiple steps to reach the desired yield and/or purity. These methods include the use of organic solvents including but not limited to lower chained alkanes such as pentane, hexane or heptane among others, chlorinated hydrocarbons like chloroform, methylene chloride or among others, aromatic hydrocarbons such as benzene or toluene among others and organic acids such as sulfonic acid or non-volatile Lewis acids such as p-toluenesulfonic acid (p-TSA), boron trifluoride, zinc chloride, zinc bromide among others and Lewis acid-solvent combinations such as hydrochloric acid in ethanol or sulfuric acid in cyclohexane. When any of these solvents or the Lewis acids mixed in with these solvents is used, persons of ordinary skill in the art must be mindful of the varying degrees of toxicity for each component. As a result, care must be taken to ensure complete removal prior to human consumption. This complicates the synthesis processes and increases the expense of production. Examples of such prior-art processes include processes disclosed in United States Patent Application Publication No. US 2004/0143126 A1.

In keeping with the rapid growth of this new industry and confronted with these rather difficult obstacles mentioned above, the need for non-toxic, solvent free, and economically competitive conversions is becoming an increasingly necessary and relevant goal to achieve.

BRIEF DESCRIPTION

Definitions and Conventions

The Scientific and technical terminology applied within the body of this invention has equal weight as is typically interpreted by persons of ordinary skill knowledgeable in the art to which this invention entails.

As used herein, CBD refers to the compound cannabidiol.

As used herein, delta-9 THC refers to the compound delta-9 tetrahydrocannabinol.

As used herein, delta-8 THC refers to the compound delta-8 tetrahydrocannabinol.

As used herein, delta-9 THC-A refers to the compound delta-9 tetrahydrocannabinolic acid.

In accordance with an aspect of the invention, methods of synthesis of delta-9 THC and delta-8 THC from CBD do not include the use of solvents.

In accordance with another aspect of the invention, methods of synthesis of delta-9 THC and delta-8 THC from cannabidiol utilize a simple mineral acid that can easily be removed by volatilization or simple neutralization to common consumable salts.

In accordance with another aspect of the invention, methods of synthesis of delta-9 THC and delta-8 THC from cannabidiol utilize non-toxic solvents in the form of natural terpenes. These solvents, found throughout the plant kingdom are to be used not necessarily for the conversion but to keep the reactants and products liquefied at temperatures below their melting point when in pure form so that the reaction may take place in an efficient manner.

In accordance with another aspect of the invention, methods are presented for synthesis of delta-9 THC and delta-8 THC from cannabidiol that is a mixture of a desired ratio of predominately delta-8 THC over delta-9 THC in a solventless environment. Ratios can approach approximately 9:1 respectively.

The present invention includes CBD as isolate, distillate, concentrates extracted from plant material or synthetically manufactured.

In accordance with an aspect of the present invention, a method for converting CBD to delta-9 THC and delta-8 THC includes adding CBD to a reaction vessel, streaming an inert gas through the reaction vessel, heating the CBD while stirring to melt the CBD, stirring the melting CBD at an elevated rpm, adding concentrated or dilute hydrochloric acid (HCl) as a catalyst to the melted CBD while stirring, increasing the temperature over time to a temperature not to exceed the boiling point of reactants and products in the reaction vessel, holding the reaction vessel at a temperature less than the boiling point temperature for the reactants and products in the reaction vessel for an amount of time to allow the complete conversion of the CBD, and bubbling an inert gas into the reaction products to remove free ions of hydrogen and chloride.

In accordance with an aspect of the invention, the CBD is heated to between about 75° C. to about 85° C.

In accordance with an aspect of the invention, the method further includes removing the acid catalyst.

In accordance with an aspect of the invention, the method further includes separating the delta-9 THC and delta-8 THC by one of chromatographic techniques and distillation techniques.

In accordance with an aspect of the invention, the method further includes analyzing all products by high performance liquid chromatography (HPLC), gas chromatography-mass spectroscopy (GC-MS) or other.

In accordance with an aspect of the invention, the method further includes analyzing the products for the presence or absence of protonated ions.

In accordance with an aspect of the invention, the method further includes analyzing the products for the presence or absence of chloride ions.

In accordance with an aspect of the invention, the CBD is one of CBD as isolate, CBD distillate concentrate extracted from plant material, and synthetically manufactured CBD.

In accordance with an aspect of the invention a method for converting CBD to delta-9 THC and delta-8 THC includes adding CBD to a reaction vessel, streaming an inert gas through the reaction vessel, heating the CBD while stirring to melt the CBD, stirring the melting CBD at an elevated rpm, adding concentrated or diluted HCl as catalyst to the melting CBD while stirring, adjusting the time, temperature and acid concentration to achieve a desired ratio of CBD to delta-9 THC to delta-8 THC, bubbling an inert gas into the reaction products to remove free ions of hydrogen and chloride, separating aqueous phase from organic phase.

In accordance with an aspect of the invention, the CBD is heated to between about 75° C. to about 85° C.

In accordance with an aspect of the invention, the method further includes neutralizing HCl using a dilute sodium hydroxide (NaOH) wash.

In accordance with an aspect of the invention, the method further includes separating the delta-9 THC and delta-8 THC by one of chromatographic techniques and distillation techniques.

In accordance with an aspect of the invention, the method further includes analyzing all products by HPLC, GC-MS or other.

In accordance with an aspect of the invention the method further includes analyzing the products for the presence or absence of protonated ions.

In accordance with an aspect of the invention, the method further includes analyzing the products for the presence or absence of chloride ions.

In accordance with an aspect of the invention, the CBD is one of CBD as isolate, CBD distillate concentrate extracted from plant material, and synthetically manufactured CBD.

In accordance with an aspect of the invention, a method for converting cannabidiol (CBD) to delta-9 THC and delta-8 THC includes adding CBD to a reaction vessel, streaming an inert gas through the reaction vessel, adding a terpene solvent, or mixture of several terpene solvents to the CBD in an amount necessary to partially or completely dissolve the CBD, stirring the CBD and solvent mixture, adding a concentrated or dilute mineral acid in minute amounts as catalyst, adjusting the time temperature and acid concentration to achieve a desired ratio of CBD to delta-9 THC to delta-8 THC, bubbling an inert gas into the reaction products to remove free ions of hydrogen and chloride, and separating aqueous phase from organic phase.

In accordance with an aspect of the invention, the method further includes separating the delta-9 THC and delta-8 THC by one of chromatographic techniques and distillation techniques.

In accordance with an aspect of the invention, the method further includes analyzing all products by HPLC, GC-MS or other.

In accordance with an aspect of the invention, the method further includes analyzing the products for the presence or absence of protonated ions.

In accordance with an aspect of the invention, the method further includes analyzing the products for the presence or absence of chloride ions.

In accordance with an aspect of the invention, the CBD is one of CBD as isolate, CBD distillate concentrate extracted from plant material, and synthetically manufactured CBD.

In accordance with an aspect of the invention, a method for converting delta-9 THC and or delta-9 THC-A to delta-8 THC includes adding at least one of delta-9 THC or delta-9 THC-A or a mixture of both to a reaction vessel, streaming an inert gas through the reaction vessel, heating at least one of delta-9 THC and delta-9 THC-A while stirring to melt the at least one of delta-9 THC and delta-9 THC-A, converting any delta-9 THC-A in the reaction vessel into delta-9 THC upon heating to initiate decarboxylation of the delta-9 THC-A, stirring the melting delta-9 THC, adding one of concentrated HCl and diluted HCl as a catalyst to the liquefied delta-9 THC while stirring, increasing the temperature over time to a temperature not to exceed the boiling point of reactants and products in the reaction vessel, holding the reaction vessel at a temperature less than the boiling point temperature for the reactants and products in the reaction vessel for an amount of time to allow the conversion of the delta-9 THC into delta-8 THC, and bubbling an inert gas into the reaction products to remove free ions of hydrogen and chloride.

In accordance with an aspect of the invention, at least one of delta-9 THC and delta-9 THC-A is heated to between about 70° C. to about 80° C.

In accordance with an aspect of the invention, the acid catalyst is removed following the conversion.

In accordance with an aspect of the invention, the method further includes separating the delta-9 THC and delta-8 THC by one of chromatographic techniques and distillation techniques.

In accordance with an aspect of the invention, the products are analyzed for the presence or absence of protonated ions.

In accordance with an aspect of the invention, the products are analyzed for the presence or absence of chloride ions.

In accordance with an aspect of the invention, the delta-9 THC is one of delta-9 THC distillate, concentrate, or delta-9 THC-A.

In accordance with an aspect of the invention, the delta-9 THC and or delta-9 THC-A is one of a plant material extract and synthetically manufactured.

BRIEF DESCRIPTION OF THE DRAWING FIGURES

The invention will be explained in more detail in the following with reference to embodiments and to the drawing in which are shown:

DETAILED DESCRIPTION

Persons of ordinary skill in the art will realize that the following description is illustrative only and not in any way limiting. Other embodiments will readily suggest themselves to such skilled persons.

Example 1

1000 grams of CBD is added to a 2-liter reaction vessel, placed in a heating mantel equipped with stirring capabilities and heated to 80° C. to melt or fluidize the CBD. At first the nitrogen gas is allowed to evacuate atmospheric gases from the reaction vessel. Nitrogen gas is allowed to stream through the reaction vessel for the duration of the reaction. After about 5 minutes of streaming nitrogen gas and as the CBD becomes fluid enough to allow the stir bar to rotate at medium speed, 350 rpm, 3 mL of 12 molar HCl is added to the CBD. The HCl settles to the bottom of the reaction flask and develops into aqueous globules floating and rotating off the bottom of the reaction vessel as a heterogeneous mixture. The temperature is slowly increased to 110° C. and the aqueous phase begins to slowly boil off as HCL and water vapors. Continued nitrogen gas streaming keeps oxygen and other gases from reentering the reaction vessel and interfering with the reaction. The streaming nitrogen gas also facilitates removal of substantially all volatized HCl and water vapors forming in the head space of the reaction vessel as the aqueous phase starts boiling off at higher and higher temperatures. If required the volatile HCl gas being carried off can be captured and measured by streaming the HCl enriched nitrogen gas into a flask of a normalized sodium hydroxide solution followed by simple titrimetric analysis.

The temperature is allowed to increase to 140° C. and held at a fixed temperature range for about 4 hours. When conversion is complete the streaming nitrogen gas is diverted into a gas dispersion tube equipped with a fritted end that is submerged into the delta-8 THC delta-9 THC concentrate to remove any free hydrogen and/or chloride ions still lingering in the product mixture.

The resulting product may be tested for pH in order to determine if any free hydrogen ions remain, and streaming may be stopped after the pH has risen to at least about 4. The pH of the final products can be less than or equal to 4.6 to be considered a high acid product and greater than or equal to 4.7 but lower than 6.9 to be considered a low acid product. Neutral pH (7.0) and alkaline pH 7.1 or greater can also be applied if neutral to basic pH is required.

Figure 1:
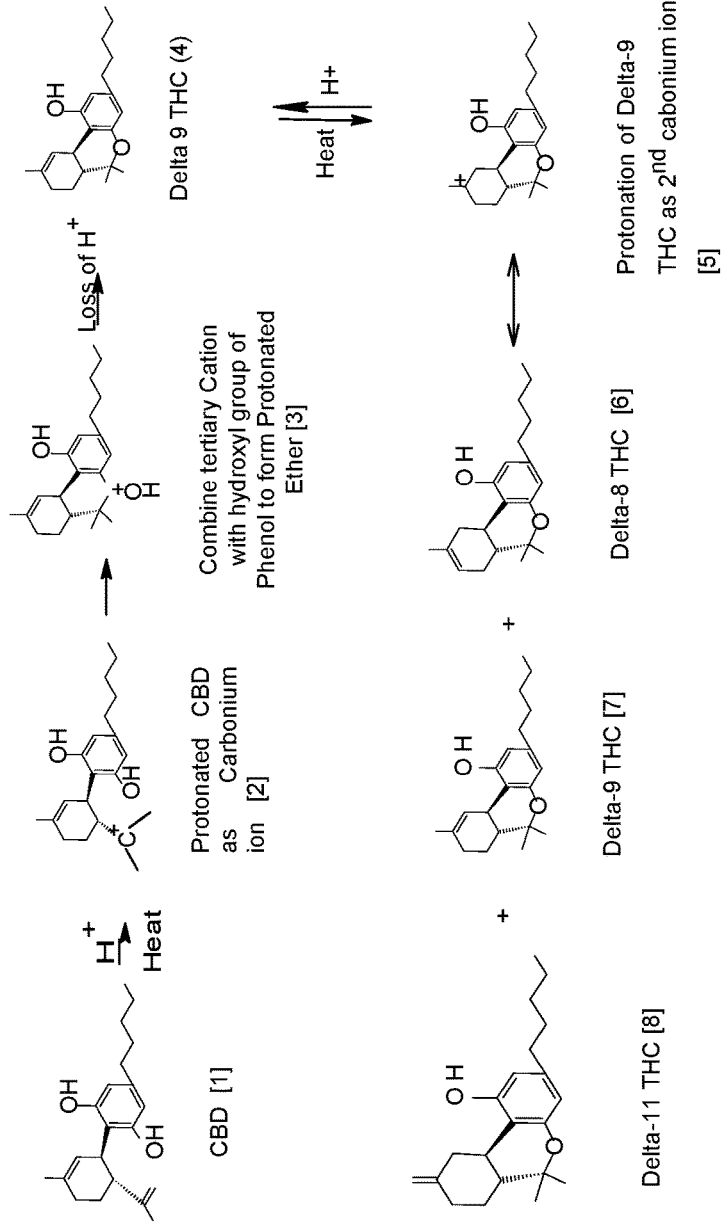
FIG. 1 is a schematic of the reaction mechanism for the conversion of CBD to delta-8 THC, delta-9 THC, and delta-11 THC.
Figure 1:
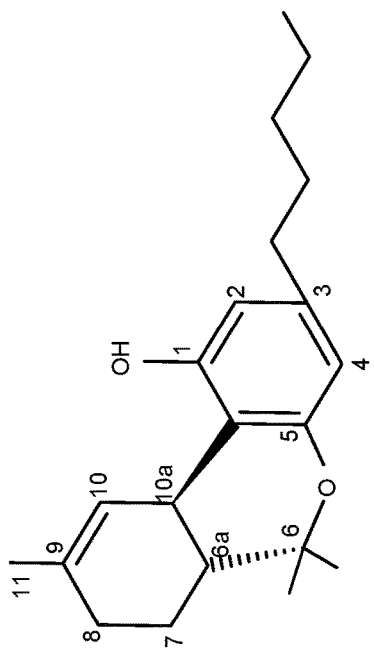
Figure 2:
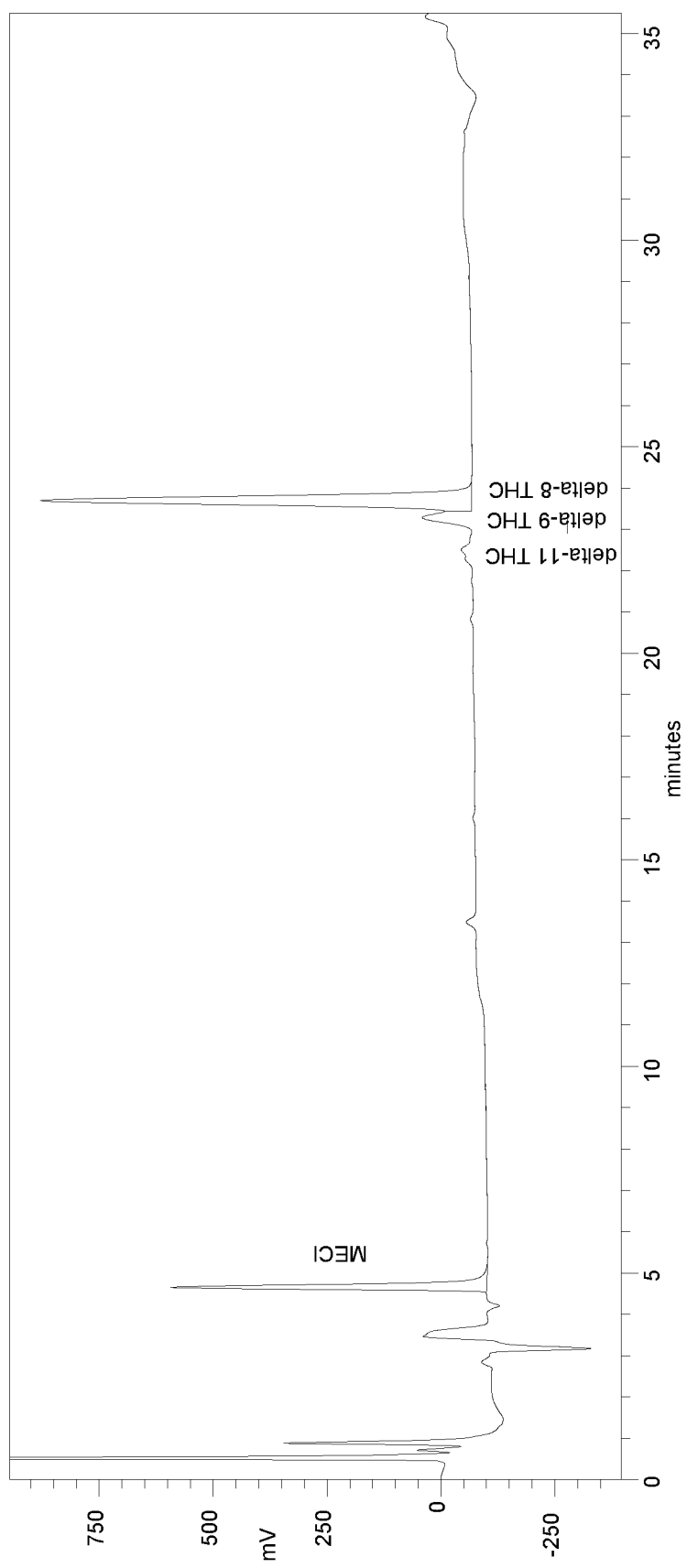
FIG. 2 is an analytical chromatogram which shows a reaction product evidencing the product ratios described in Example 1 herein.

After several hours the gas dispersion tube, stir bar and heat is removed and while still warm the contents are transferred to a suitable container for storage. Typical yields of the various THC isomers based on 1000 grams of starting material are approximately 89% for delta-8 THC or 890 grams and 9% or 90 grams of delta-9 THC. FIG. 2 shows an example chromatographic analysis of this product mixture with the delta-9 THC peak showing at 23.3 minutes and the delta-8 THC peak showing at 23.9 minutes retention times. FIG. 1 shows a supporting schematic for the conversion of CBD to delta-8 and delta-9 THC utilizing heat and acid.

A quantitative analysis for chlorides can be accomplished via ion chromatography or ion selective electrode. But it may be reasonable to assume that the volatile chlorides have been vaporized at these higher temperatures. The delta-9 THC and delta-8 THC can be used as is, separated further by commonly known chromatographic techniques into their various isomeric forms, or subsequently be used in the formulation and preparation of a large variety of consumable products.

The reaction described in Example 1 can be conducted at all temperatures between the melting point of CBD, 66° C., and the boiling point of CBD and the other reaction products 157° C. to 180° C. The stir bar may be rotated at between about 300 rpm and about 400 rpm. The amount of 12 molar HCl that is added to the CBD can vary from about 2 mL to about 3 mL. The slow temperature increase after adding the HCl may be from between 100° C. to about 110° C.

Temperature vs. time for conversion can also be adjusted by conducting the reaction described in Example 1 under various pressures from 1 atmosphere to several atmospheres with or without sonication.

Increasing the pressure will allow the reaction to progress at higher temperatures and increase the reaction rate thereby reducing the time interval for complete conversion.

Adding sonication aids in the agitation and ultimate dispersion of the aqueous phase into the organic phase forming a semi-emulsion which will increase the reaction rate, shortening the time interval for complete conversion.

Referring now to FIG. 1, a diagram illustrates the chemical reactions that take place during the conversion processes described with reference to Examples 1, 2, and 3. FIG. 2 is an analytical chromatogram which shows a reaction product evidencing the product ratios described in Example 1 herein.

Example 2

1000 grams of CBD is added to a 2-liter reaction vessel, placed in a heating mantel equipped with stirring capabilities and heated to 80° C. to melt or fluidize the CBD. At first the nitrogen gas evacuates atmospheric gases from the reaction vessel. Nitrogen gas then streams through the reaction vessel for the duration of the reaction in order to keep atmospheric gases out. After about 5 minutes of streaming nitrogen gas and when the CBD becomes fluid enough to allow the stir bar to rotate at medium speed, 350 rpm, 3 mL of concentrated or dilute HCl acid is added to the CBD. The HCl is now submerged to the bottom of the reaction flask and develops into small aqueous globules floating and rotating off the bottom of the reaction vessel as a heterogeneous mixture. The temperature is allowed to remain constant for the duration of the process to allow the delta-9 THC isomer which forms first to dominate over the delta-8 THC isomer. As long as the CBD concentration remains the predominate compound (greater than 50%) in the reaction vessel the delta-9 THC isomer will be first to form. As the CBD concentration continues to decline below 50% the delta-9 THC isomer will continue to be the first conversion but the excess hydronium ion will, with increasing frequency, attack the tertiary carbon on the delta-9 THC isomer initiating rearrangement to the delta-8 THC isomer. Continued nitrogen gas streaming keeps oxygen and other gases from reentering the reaction vessel and interfering with the reaction. While the reaction proceeds a small subsample is periodically recovered to test by HPLC. When the desired ratio of CBD to delta-9 THC to delta-8 THC is reached (42%, 32%, 26%) in this example a ratio of roughly 4:3:3, the remaining aqueous phase is removed first by evacuating as much of the bottom phase as possible by submerged vacuum pumping into a separatory funnel. Next the streaming nitrogen gas is diverted into a gas dispersion tube equipped with a fritted end that is submerged into the delta-8 THC and delta-9 THC mixture and remaining CBD to remove any free hydrogen and/or chloride ions still lingering in the product mixture. The aqueous phase removed from the bottom of the reaction vessel can be neutralized and discarded. After several hours of bubbling nitrogen gas through the CBD, THC products a pH test of a sub sample is conducted to determine the absence or presence of residual hydrogen ions.

Figure 3:
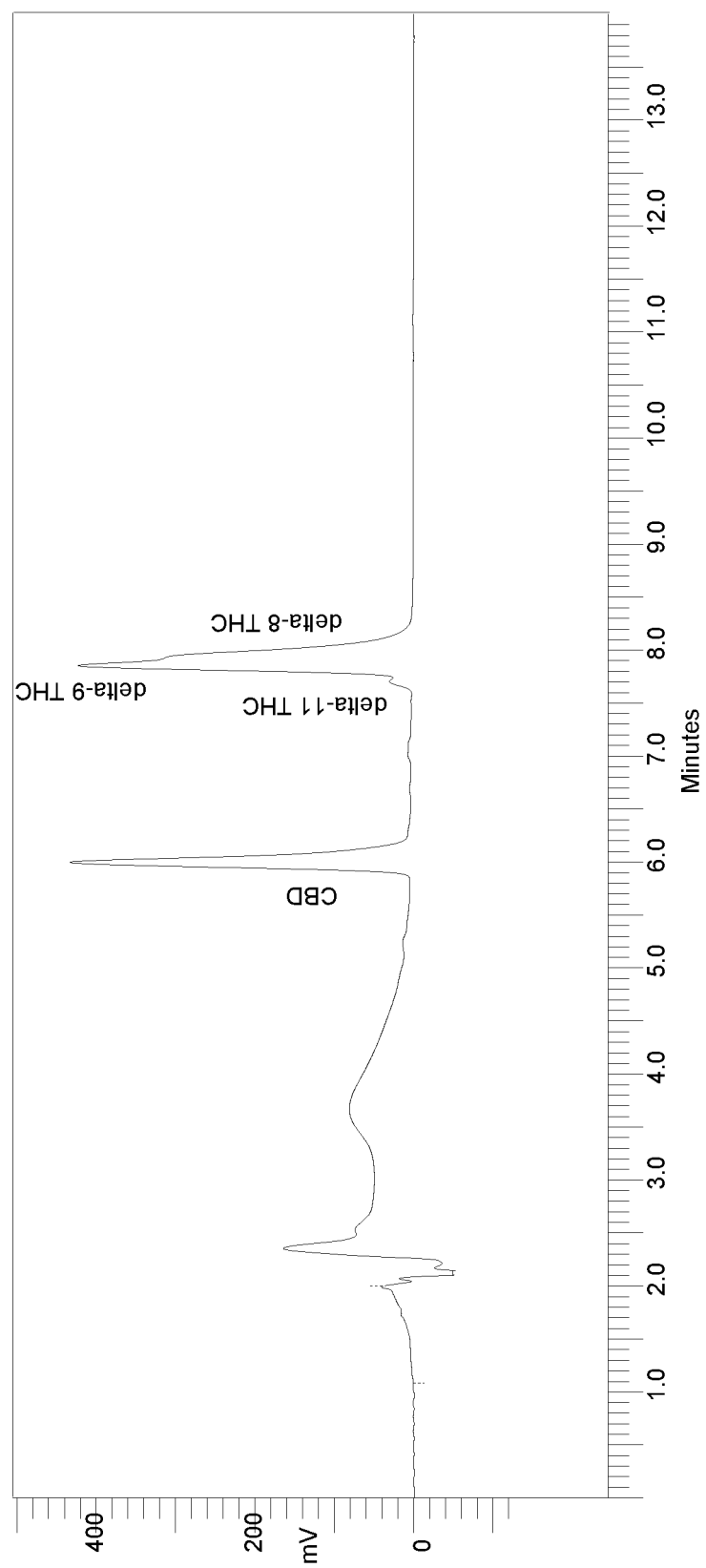
FIG. 3 is an analytical chromatogram which shows a reaction product evidencing the product ratios shown in Example 2 herein.

If excess hydrogen ions are still present bubbling of nitrogen gas is continued until a desired pH of about 4 is achieved, after which the gas dispersion tube, the stir bar and heat are removed and while still warm the contents are transferred to a suitable container for storage. A typical product yield based on 1000 grams of starting material is 32% delta-9 THC (320 grams), 26% delta-8 THC or 260 grams and 42% or 420 grams of CBD. FIG. 3 shows an example chromatographic analysis of this product mixture with the CBD peak showing at 6.0 minutes, the delta-9 THC peak showing at 7.9 minutes, and the delta-8 THC peak showing at 8.1 minutes retention times. FIG. 1 shows a supporting schematic for the conversion of CBD to delta-8 and delta-9 THC utilizing heat and acid.

It may become desirable or necessary to separate the CBD and the THC compounds from each other. Common chromatographic techniques can be used to accomplish this. Any excess CBD that has not been converted can be recycled into future conversions and the delta-9 THC delta-8 THC can be used as is, separated further into their various isomeric forms by chromatographic techniques, distillation or other separation method. The delta-9 THC delta-8 THC mixture can also be used in the formulation and preparation of a large variety of consumable products.

The reaction described in Example 2 can be conducted at all temperatures between the melting point of CBD, 66° C., and the boiling point of CBD and the other reaction products 157° C. to 180° C. with similar results.

Temperature vs. time for conversion can also be adjusted by conducting the reaction described in Example 2 under various atmospheric pressures from 1 atmosphere to several atmospheres with or without sonication.

Increasing the pressure will allow the reaction to progress at higher temperatures which will increase the reaction rate and reduce the time interval required for conversion.

Adding sonication aids in the agitation and ultimate dispersion of the aqueous phase into the organic phase forming a semi-emulsion which will increase the reaction rate, shortening the time interval for conversion.

FIG. 3 is an analytical chromatogram which shows a reaction product evidencing the product ratios described in Example 2 herein.

Example 3

1000 grams of CBD is added to a 2-liter reaction vessel, placed in a heating mantel equipped with stirring capabilities. Terpene (d-limonene preferred) is added to begin to dissolve the CBD which can approach a ratio of 3:1 ratio wt/wt CBD to terpene respectively at lower temperatures (34° C.). Nitrogen gas is used to evacuate atmospheric gases from the reaction vessel. After about 5 minutes of streaming nitrogen gas and when the CBD/terpene mixture becomes fluid enough to allow the stir bar to rotate, 2 mL of concentrated or dilute hydrochloric acid (HCl) catalyst is added to the CBD/terpene mixture. While streaming nitrogen gas through the reaction vessel begin sealing off all exit ports and reduce nitrogen flow until stopped. The reaction vessel is now maintained as a closed system with very slight pressure from nitrogen gas. The hydrochloric acid settles to the bottom of the reaction flask and develops into small aqueous globules floating and rotating off the bottom of the reaction vessel as a heterogeneous mixture. Care must be taken when using higher temperatures approaching the CBD melting point of 66° C. with frequent testing for the concentration of CBD, delta-9 THC, delta-8 THC and d-limonene by HPLC.

The preferred reaction temperature is 38° C., but temperature can be maintained anywhere between the freezing point of the terpene used (e.g., d-limonene melting point is −59° C.) and the melting point of CBD isolate (66° C.) depending on allotted reaction time, amount of catalyst added and products desired. Using temperatures below 38° C. approaching 0° C. increases the time needed for conversion from days to weeks or even months. Using temperatures above 38° C. approaching 70° C. decreases the time needed for conversion from several days down to 24 hours or less. The temperature does not have to remain constant to allow the delta-9 THC isomer to dominate over the delta-8 THC isomers.

After some time when the desired ratio of CBD to delta-9 THC to delta-8 THC is reached, the reaction is stopped. As stated in Example 2 so long as the CBD concentration remains the predominate compound (greater than 50%) in the reaction vessel the delta-9 THC isomer will be first to form and dominate the THC isomer series.

After the desired products ratio are obtained the remaining aqueous phase is removed first by evacuating as much of the bottom phase as possible (submerged vacuum pumping into separatory funnel). Next, a closed port is reopened and the streaming nitrogen gas is diverted into a gas dispersion tube equipped with a fritted end that is submerged into the delta-9 THC, delta-8 THC, and remaining CBD to remove any free hydrogen and/or chloride ions still lingering in the product mixture.

Figure 4:
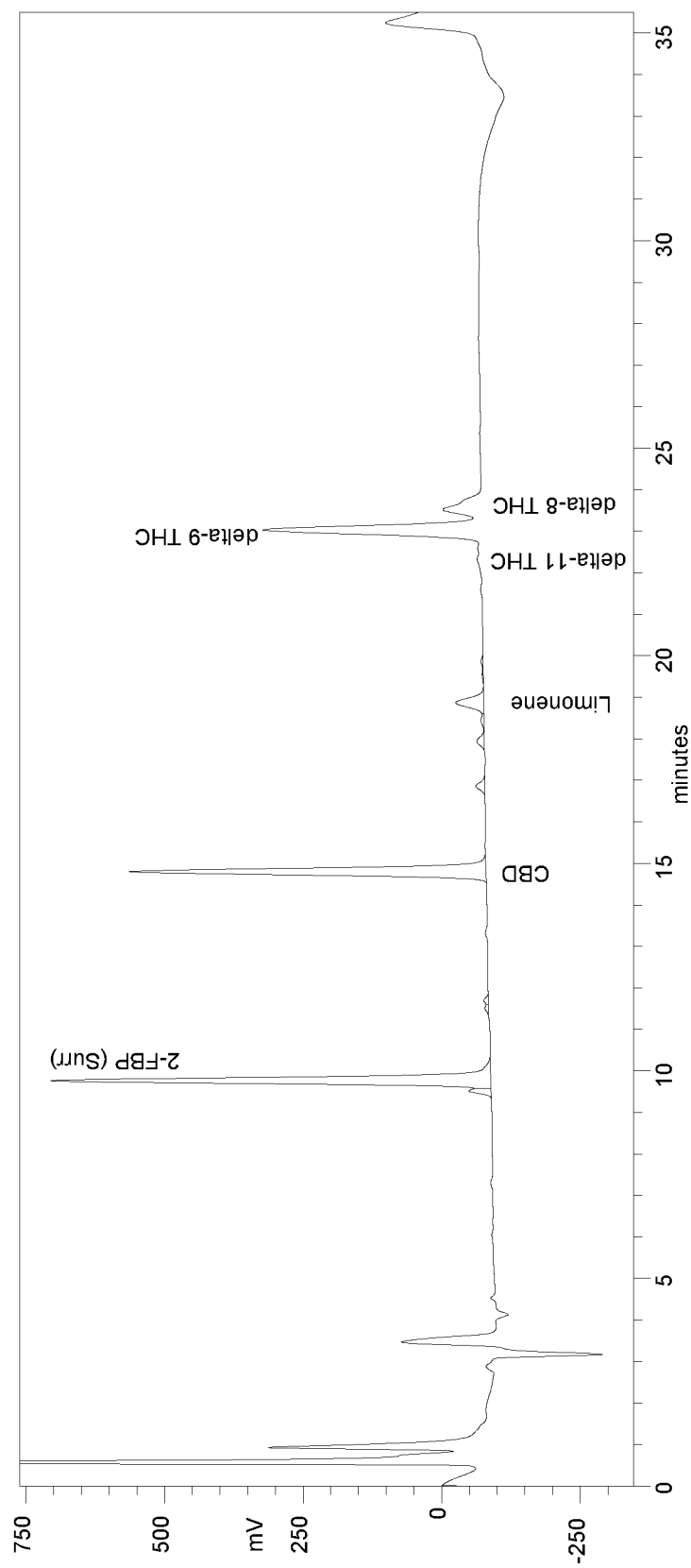
FIG. 4 is an analytical chromatogram which shows a reaction product evidencing the product ratios shown in Example 3 herein.

A pH and chloride test of the organic phase is carried out to quantify the amount of remaining chloride and hydrogen ions. If the final product is still below a pH of 5 a gas dispersion tube is submerged into the product and nitrogen gas is streamed through the tube allowing for the nitrogen gas bubbles to scrub any lingering protons or chloride ions out of the product. A typical product yield based on 1000 grams of starting material, excluding the terpene used, is 41% delta-9 THC (410 grams), 8% delta-8 THC or 80 grams and 51% or 510 grams of CBD (510 grams). FIG. 4 shows an example chromatographic analysis of this product mixture with the CBD peak showing at 14.9 minutes, the delta-9 THC peak showing at 23.2 minutes, and the delta-9 THC peak showing at 23.8 minutes retention times. FIG. 1 shows a supporting schematic for the conversion of CBD to delta-8 and delta-9 THC utilizing heat and acid.

In instances where temperatures approach 30° C. or lower the terpenes used may be too concentrated in the final product and it may become desirable or necessary to remove some or all of the terpene solvent. Common chromatographic techniques can be used to accomplish this. Any excess CBD that has not been converted can also be removed from the final product and recycled into the next batch along with the terpenes using similar chromatographic techniques and the delta-9 THC delta-8 THC can be used as is, separated further, or subsequently be used in the formulation and preparation of a large variety of consumable products.

In accordance with the methods of the present invention, a vacuum may be employed to decrease the boiling point of the components with the goal of removing certain volatiles, such as HCl and other acids, water vapor, etc. at lower temperatures. The reactions may also be conducted under vacuum with ultrasonic energy added to aid in removal of volatiles.

In accordance with the present invention, mixing methods may include stir bar, impeller, ultrasonic agitation, or other commonly used mixing methods.

FIG. 4 is an analytical chromatogram which shows a reaction product evidencing the product ratios described in Example 3 herein.

Example 4

Figure 5:
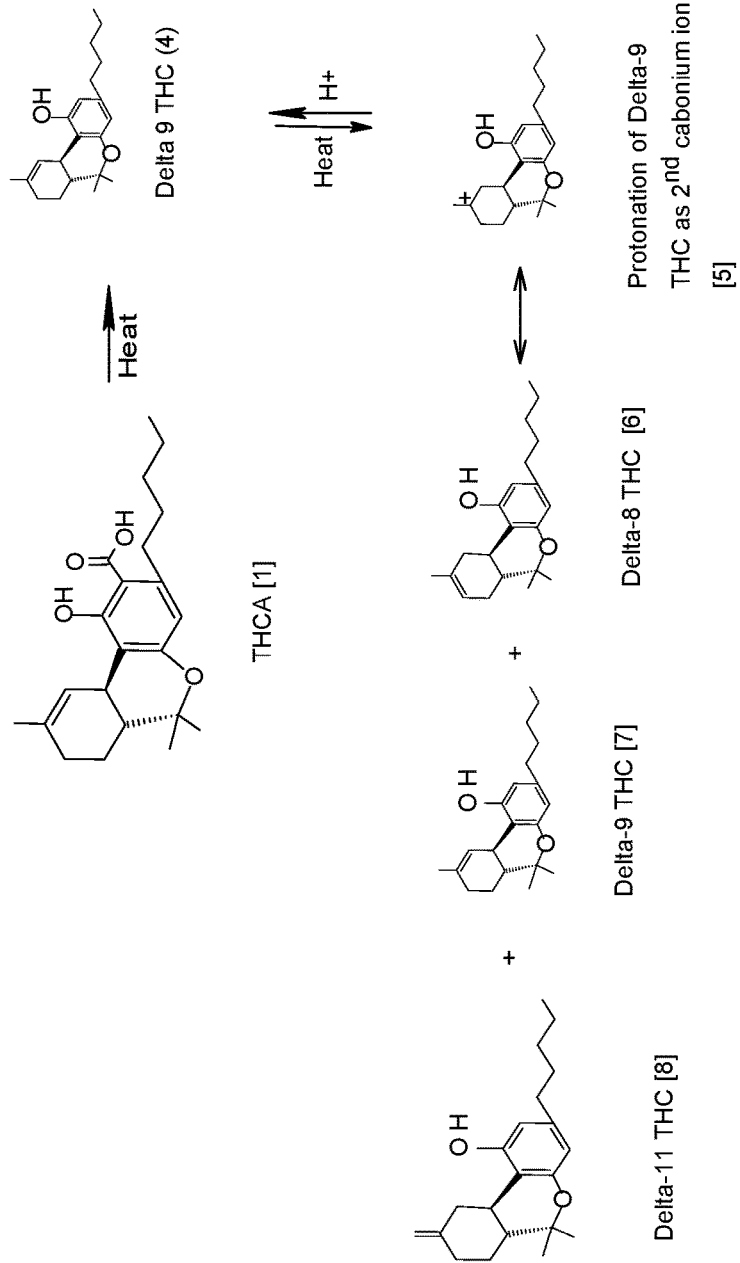
FIG. 5 is a schematic of the reaction mechanism for the conversion of THCA or delta-9 THC to delta-8 THC, delta-9 THC, and delta-11 THC.
Figure 5:
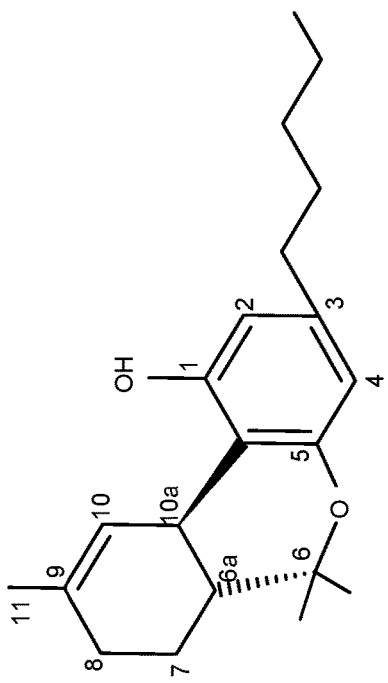

1000 grams of delta-9 THC and or delta-9 THC-A as concentrate, distillate or other is added to a 2-liter reaction vessel, placed in a heating mantel equipped with stirring capabilities and heated to between 80° C. to melt or fluidize the delta-9 THC. At first the nitrogen gas is allowed to evacuate atmospheric gases from the reaction vessel. Nitrogen gas is allowed to stream through the reaction vessel for the duration of the reaction. After about 5 minutes of streaming nitrogen gas and as the delta-9 THC becomes fluid enough to allow the stir bar to rotate at medium speed, 350 rpm, 3 mL of 12M HCl is added to the delta-9 THC. The HCl settles to the bottom of the reaction flask and develops into aqueous globules floating and rotating off the bottom of the reaction vessel as a heterogeneous mixture. The temperature is slowly increased to 110° C. and the aqueous phase begins to slowly boil off as HCL and water vapors. Continued nitrogen gas streaming keeps oxygen and other gases from reentering the reaction vessel and interfering with the reaction. The streaming nitrogen gas also facilitates removal of substantially all volatized HCl and water vapors forming in the head space of the reaction vessel as the aqueous phase starts boiling off at higher and higher temperatures. FIG. 5 shows a supporting schematic for the initial conversion of THCA to delta-9 THC utilizing heat, and then from delta-9 THC to the other THC isomers while utilizing heat and acid.

Figure 6:
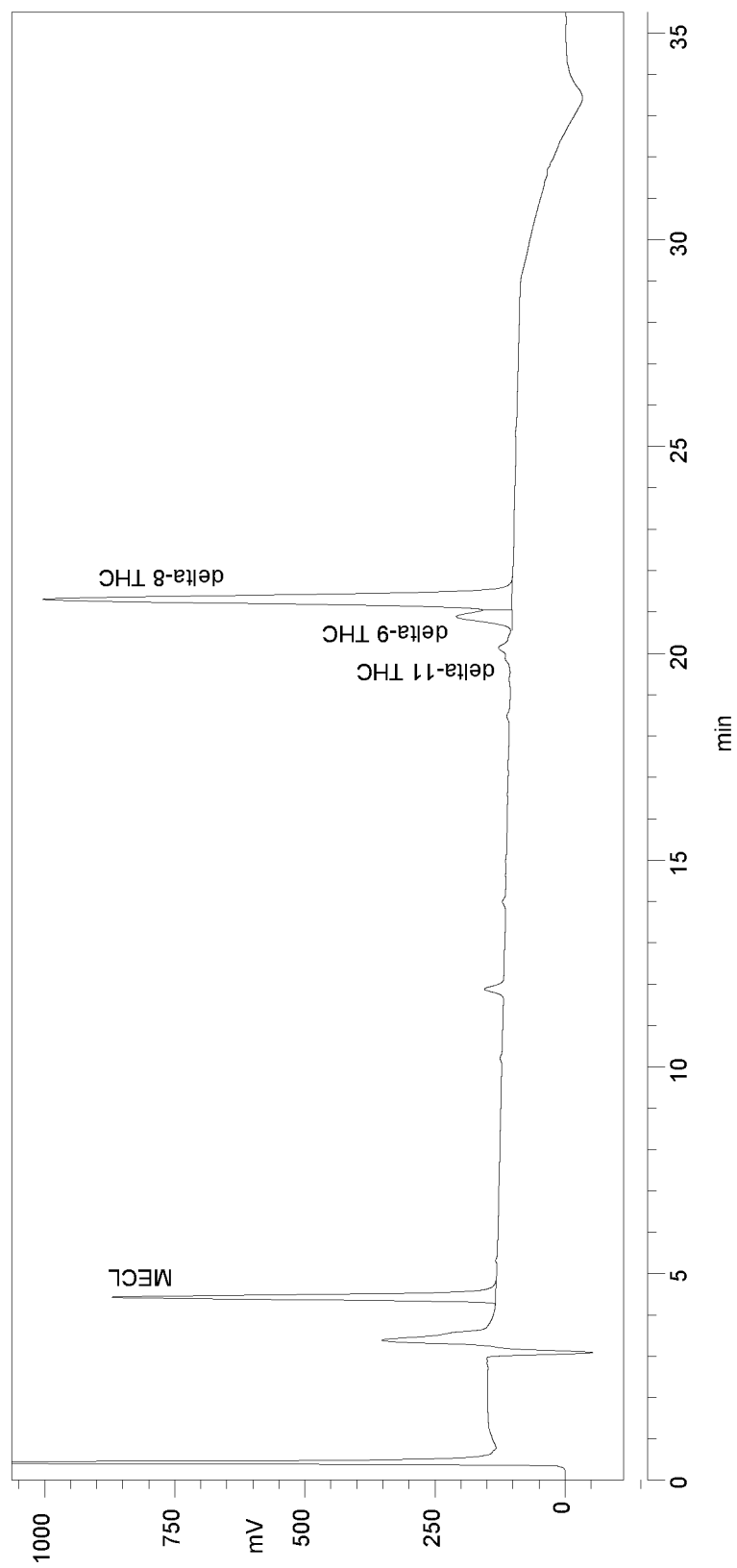
FIG. 6 is an analytical chromatogram which shows a reaction product evidencing the product ratios shown in Example 4 herein.

The temperature is allowed to increase to 140° C. and held at this temperature range for about 3 to 4 hours. When conversion is complete the streaming nitrogen gas is diverted into a gas dispersion tube equipped with a fritted end that is submerged into the delta-8 THC delta-9 THC concentrate to remove any free hydrogen and/or chloride ions still lingering in the product mixture. After several hours the gas dispersion tube, stir bar and heat is removed and while still warm the contents are transferred to a suitable container for storage. Based on 1,000 grams of delta-9 THC-A starting material, typical yields of the delta-8 THC isomer converted from the delta-9 THC isomer are approximately 88% for delta-8 THC or 880 grams while 11% or 110 grams of delta-9 THC remains unconverted beyond the delta-9 THC-A decarboxylation or it is in chemical equilibrium with the D-8 isomer. FIG. 6 shows an example chromatographic analysis of this product mixture with the delta-9 THC peak showing at 21.0 minutes, and the delta-8 THC peak showing at 21.4 minutes retention times.

If required, the volatile HCl gas being carried off during nitrogen streaming can be captured and measured by streaming the HCl enriched nitrogen gas into a flask of a normalized sodium hydroxide (NaOH) solution followed by simple titrimetric analysis.

The resulting product may be tested for pH in order to determine if any free hydrogen ions remain, and streaming may be stopped after the pH has risen to at least about 5.

A quantitative analysis for chlorides can be accomplished via ion chromatography or ion selective electrode. But it may be reasonable to assume that the volatile chlorides have been vaporized at these higher temperatures. The delta-8 THC and delta-9 THC can be used as is, separated further by commonly known chromatographic techniques into their various isomeric forms, or subsequently be used in the formulation and preparation of a large variety of consumable products.

The reaction illustrated in Example 4 can be conducted at all temperatures up to and including the boiling point of the delta-9 THC and delta-8 THC reaction products (155° C. to 180° C.) so long as the starting material, delta-9 THC is fluid enough for the acid catalyst to come in contact with and react with the delta-9 THC in this heterogeneous environment. The preferred temperature ranges listed in the discussion following example 1 are the presently preferred temperature ranges.

Temperature vs. time for conversion can also be adjusted by conducting the reaction under various pressures from 1 atmosphere to several atmospheres with or without sonication.

Increasing the pressure will allow the reaction to progress at higher temperatures and increase the reaction rate thereby reducing the time interval for complete conversion.

Adding sonication aids in the agitation and ultimate dispersion of the aqueous phase into the organic phase forming a semi-emulsion which will increase the reaction rate, shortening the time interval for complete conversion.

Referring now to FIG. 5, a diagram illustrates the chemical reactions that take place during the conversion processes described with reference to Example 4. FIG. 6 is an analytical chromatogram which shows a reaction product evidencing the product ratios described in Example 4 herein.

Careful review and interpretation of the chromatographic analytical results suggest to the inventors that a third THC isomer may be present in the product mixtures for all 4 Examples. Just before the delta-9 THC and delta-8 THC chromatogram peaks a small peak appears each time the methods are performed. Although additional analytical test work is needed to confirm this third isomer it is suggested by the inventors to be delta-11 THC isomer. Reinforcement of this suggested third isomer is due to formation of the carbonium ion at the C-9 carbon. Rearrangement frequently occurs forming the more thermodynamically stable delta-8 THC isomer. It is also possible that rearrangement to the delta-11 THC isomer occurs. FIG. 3 shows a chromatographic example of the D11 isomer chromatographic peak in at a retention time of 7.2 minutes. In additional support of this conclusion, FIG. 1 and FIG. 5 show the reaction schematic whereby Delta-11 THC is produced along with the other THC isomers from CBD or delta-9 THC utilizing heat and acid.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A method for converting CBD to delta-9 THC and delta-8 THC comprising:
    adding CBD to a reaction vessel;
    streaming an inert gas through the reaction vessel;
    heating the CBD while stirring to melt the CBD;
    stirring the melting CBD;
    adding concentrated hydrochloric acid as a catalyst to the melting CBD while stirring;
    increasing the temperature over time to a temperature not to exceed the boiling point of reactants and products in the reaction vessel;
    holding the reaction vessel at a temperature less than the boiling point temperature for the reactants and products in the reaction vessel for an amount of time to allow the complete conversion of the CBD; and
    bubbling an inert gas into the reaction products to remove free ions of hydrogen and chloride.

2. The method of claim 1 wherein heating the CBD while stirring to melt the CBD comprises heating the CBD to between about 75° C. to about 85° C.

3. The method of claim 1 further comprising removing the acid catalyst.

4. The method of claim 1 further comprising separating the delta-9 THC and delta-8 THC by one of chromatographic techniques and distillation techniques.

5. The method of claim 1 further comprising analyzing all products by one of HPLC and GC-MS.

6. The method of claim 1 further comprising analyzing the products for the presence or absence of protonated ions.

7. The method of claim 1 further comprising analyzing the products for the presence or absence of chloride ions.

8. The method of claim 1 wherein the CBD is one of CBD as isolate, distillate, concentrate, and the CBD is extracted from plant material or is synthetically manufactured.

9. A method for converting CBD to delta-9 THC and delta-8 THC comprising:
    adding CBD to a reaction vessel;
    streaming an inert gas through reaction vessel;
    heating the CBD while stirring to melt the CBD;
    stirring the melting CBD at an elevated rpm;
    adding concentrated hydrochloric acid as catalyst to the melting CBD while stirring;
    adjusting the time, temperature, and acid concentration to achieve any desired ratio of CBD to delta-9 THC to delta-8 THC;
    bubbling an inert gas into the reaction products to remove free ions of hydrogen and chloride; and
    separating an aqueous phase from an organic phase.

10. The method of claim 9 wherein heating the CBD while stirring to melt the CBD comprises heating the CBD to between about 75° C. to about 85° C.

11. The method of claim 9 further comprising neutralizing HCl using a dilute sodium hydroxide wash.

12. The method of claim 9 further comprising separating the delta-9 THC and delta-8 THC by one of chromatographic techniques and distillation techniques.

13. The method of claim 9 further comprising analyzing all products by one of HPLC and GC-MS.

14. The method of claim 9 further comprising analyzing the products for the presence or absence of protonated ions.

15. The method of claim 9 further comprising analyzing the products for the presence or absence of chloride ions.

16. The method of claim 9 wherein the CBD is one of CBD as isolate, CBD distillate concentrate, extracted from plant material, and synthetically manufactured CBD.

17. A method for converting CBD to delta-9 THC and delta-8 THC comprising:
    adding CBD to a reaction vessel;
    streaming an inert gas through reaction vessel;
    adding a terpene solvent or a mixture of several terpene solvents to the CBD in an amount necessary to partially or completely dissolve the CBD;
    stirring the CBD and solvent mixture;
    adding a concentrated or dilute mineral acid in minute amounts as catalyst;
    adjusting the time, temperature, and acid concentration to achieve a desired ratio of CBD to delta-9 THC to delta-8 THC;
    bubbling an inert gas into the reaction products to remove free ions of hydrogen and chloride; and
    separating an aqueous phase from an organic phase.

18. The method of claim 17 further comprising neutralizing HCl using a dilute NaOH wash.

19. The method of claim 17 further comprising separating the delta-9 THC and delta-8 THC by one of chromatographic techniques and distillation techniques.

20. The method of claim 17 further comprising analyzing all products by one of HPLC and GC-MS.

21. The method of claim 17 further comprising analyzing the products for the presence or absence of protonated ions.

22. The method of claim 17 further comprising analyzing the products for the presence or absence of chloride ions.

23. The method of claim 17 wherein the CBD is one of CBD as isolate, CBD distillate concentrate, extracted from plant material, and synthetically manufactured CBD.

24. The method of claim 22 wherein the delta-9 THC is one of a plant material extract and synthetically manufactured.

* * * * *